(12) United States Patent
Minoguchi et al.

(10) Patent No.: US 7,994,387 B2
(45) Date of Patent: Aug. 9, 2011

(54) TAMPON HAVING ZONED APERTURED OVERWRAP

(75) Inventors: Ryo Minoguchi, Cincinnati, OH (US); Kelyn Anne Arora, Cincinnati, OH (US); Letha Margie Hines, Cincinnati, OH (US); Ricky Alan Pollard, Moscow, OH (US); Karen Denise McAffry, Cincinnati, OH (US); John Richard Noel, Cincinnati, OH (US)

(73) Assignee: The Procter & Gamble Company, Cincnnati, OH (US)

( * ) Notice: Subject to any disclaimer, the term of this patent is extended or adjusted under 35 U.S.C. 154(b) by 0 days.

(21) Appl. No.: 11/873,589

(22) Filed: Oct. 17, 2007

(65) Prior Publication Data
US 2009/0105678 A1    Apr. 23, 2009

(51) Int. Cl.
A61F 13/15    (2006.01)
A61F 13/20    (2006.01)

(52) U.S. Cl. .............. 604/383; 604/385.17; 604/385.18; 604/379

(58) Field of Classification Search .................. 604/379, 604/383, 385.04
See application file for complete search history.

(56) References Cited

U.S. PATENT DOCUMENTS

| | | | |
|---|---|---|---|
| 2,057,206 A | 10/1936 | Pohl | |
| 3,081,515 A | 3/1963 | Griswold et al. | |
| 3,345,243 A * | 10/1967 | Kalwaites | 428/131 |
| 4,381,783 A | 5/1983 | Elias | |
| 4,908,026 A * | 3/1990 | Sukiennik et al. | 604/378 |
| 5,542,914 A | 8/1996 | Van Iten | |
| 5,591,149 A * | 1/1997 | Cree et al. | 604/378 |
| 5,714,107 A | 2/1998 | Levy et al. | |
| 6,007,498 A * | 12/1999 | Buck et al. | 600/572 |
| 6,174,293 B1 * | 1/2001 | Buck et al. | 600/572 |
| 6,203,654 B1 * | 3/2001 | McFall et al. | 156/268 |
| 6,319,239 B1 * | 11/2001 | Daniels et al. | 604/385.01 |
| 6,452,064 B1 * | 9/2002 | Thoren et al. | 604/383 |
| 6,465,713 B1 | 10/2002 | Gell et al. | |
| 6,548,731 B2 * | 4/2003 | Mizutani et al. | 604/365 |
| 6,570,055 B2 | 5/2003 | Yang et al. | |

(Continued)

FOREIGN PATENT DOCUMENTS

EP    1 481 656 A1    12/2004

(Continued)

OTHER PUBLICATIONS

PCT International Search Report dated Apr. 23, 2009.

*Primary Examiner* — Leslie R Deak
*Assistant Examiner* — Susan Su
(74) *Attorney, Agent, or Firm* — Andrew J. Hagerty; Amanda T. Barry

(57) ABSTRACT

Tampons having a zoned apertured overwrap. The tampons can include a compressed absorbent member having an insertion end, a withdrawal end, a longitudinal axis, and a body disposed between the insertion end and the withdrawal end. The body can have a perimeter disposed substantially perpendicularly to the longitudinal axis and an exterior surface. The tampons can further include an overwrap covering at least a portion of the exterior surface. The overwrap can have a first zone and a second zone, the first zone having a plurality of apertures of a first diameter and the second zone having a plurality of apertures of a second diameter. In addition, the first zone and the second zone can be spaced apart from one another.

14 Claims, 4 Drawing Sheets

U.S. PATENT DOCUMENTS

| | | | |
|---|---|---|---|
| 6,582,798 B2 * | 6/2003 | Thomas | 428/132 |
| 6,649,807 B2 * | 11/2003 | Mizutani | 604/367 |
| 6,743,965 B2 * | 6/2004 | Yang et al. | 604/367 |
| 6,818,802 B2 * | 11/2004 | Takai et al. | 604/383 |
| 6,860,874 B2 | 3/2005 | Gubernick et al. | |
| 6,888,046 B2 * | 5/2005 | Toyoshima et al. | 604/380 |
| 6,916,969 B1 * | 7/2005 | Helmfridsson et al. | 604/378 |
| 7,005,558 B1 * | 2/2006 | Johansson et al. | 604/383 |
| 2001/0014348 A1 | 8/2001 | Schoelling | |
| 2002/0142693 A1 | 10/2002 | Buzot | |
| 2003/0093049 A1 * | 5/2003 | Johnson et al. | 604/370 |
| 2003/0097108 A1 * | 5/2003 | Hasse et al. | 604/379 |
| 2003/0097112 A1 | 5/2003 | Gilbert et al. | |
| 2003/0125687 A1 | 7/2003 | Gubernick et al. | |
| 2003/0167044 A1 * | 9/2003 | Toyoshima et al. | 604/367 |
| 2003/0171730 A1 * | 9/2003 | Kelly et al. | 604/383 |
| 2004/0030316 A1 * | 2/2004 | Gubernick et al. | 604/383 |
| 2004/0049167 A1 | 3/2004 | Hasse et al. | |
| 2004/0259707 A1 * | 12/2004 | Lochte et al. | 492/30 |
| 2005/0113807 A1 * | 5/2005 | Carlin | 604/904 |
| 2005/0177090 A1 * | 8/2005 | Jensen | 604/14 |
| 2005/0187531 A1 * | 8/2005 | Alcantara et al. | 604/385.04 |
| 2005/0228353 A1 * | 10/2005 | Thomas | 604/385.01 |
| 2006/0019063 A1 | 1/2006 | Kelly | |
| 2006/0217677 A1 | 9/2006 | Chase et al. | |
| 2006/0241556 A1 * | 10/2006 | Lochte et al. | 604/378 |
| 2008/0064581 A1 * | 3/2008 | Lochte et al. | 492/35 |

FOREIGN PATENT DOCUMENTS

| | | | |
|---|---|---|---|
| GB | 2227666 A | * | 8/1990 |
| JP | 11155902 | * | 6/1999 |
| JP | 2003070836 | * | 3/2003 |
| WO | WO 2007/114742 A1 | | 10/2007 |

* cited by examiner

TAMPON HAVING ZONED APERTURED OVERWRAP

FIELD OF THE INVENTION

The invention relates to tampons having an apertured overwrap, and more particularly to tampons having a zoned apertured overwrap.

BACKGROUND OF THE INVENTION

Tampons for feminine hygiene are typically used within a woman's vagina to absorb body exudates, such as menstrual fluids. Tampons are generally categorized by absorbency level to enable women to select a tampon that provides optimal leakage protection, that is, the tampon should prevent menstrual discharges from leaking out of the user's body. Absorbency level is generally regulated and publicized, such as, e.g., on the tampon package, wrapper, and/or applicator of the tampon, to assist women in selecting the proper tampon. Women often experience unexpected leakage, however, even though they believe they have chosen a tampon with the correct absorbency level. This unexpected leakage can contribute to a feeling of anxiety in the consumer during use.

Because tampons are typically used within a woman's vagina, a user generally cannot evaluate how the tampon is performing during use by viewing the tampon. Instead, a user may evaluate the effectiveness of the tampon based on whether or not the user experiences leakage. A user may also evaluate effectiveness of the tampon based on the appearance of the tampon after use and/or before use. For example, a user may view the tampon post-use to determine the distribution of menstrual fluid within the tampon and/or may view the tampon pre-use to visually identify any leakage protection features that may be apparent. Thus, tampon appearance can provide information to a user that can potentially alleviate feelings of anxiety with respect to unexpected leakage.

As such, it would be desirable to provide a tampon having improved leakage protection. It would also be desirable to provide a tampon having an improved visual appearance before and/or after use.

SUMMARY OF THE INVENTION

Tampons having a zoned apertured overwrap are provided. The tampons can include a compressed absorbent member having an insertion end, a withdrawal end, a longitudinal axis, and a body disposed between the insertion end and the withdrawal end. The body can have a perimeter disposed substantially perpendicularly to the longitudinal axis and an exterior surface. In certain embodiments, the tampons can include an overwrap covering at least a portion of the exterior surface. The overwrap can have a first zone and a second zone, the first zone having a plurality of apertures of a first diameter and the second zone having a plurality of apertures of a second diameter. In addition, the first zone and the second zone can be spaced apart from one another.

Also provided are tampons having an overwrap including at least one extension extending beyond the body of the tampon along the longitudinal axis. In certain embodiments, the extension can be substantially aperture-free.

DETAILED DESCRIPTION OF THE INVENTION

Figure 1:
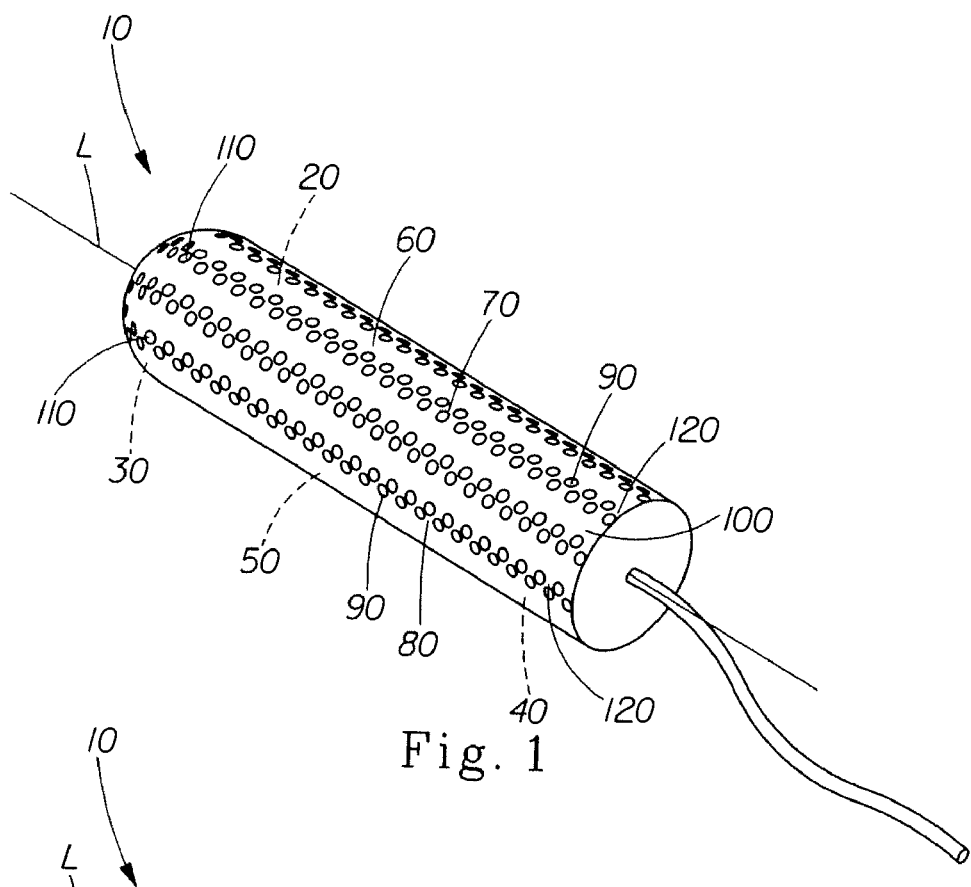
FIG. 1 is a perspective view of one embodiment of the present invention.

The present invention relates to tampons that include a zoned apertured overwrap. Such zones can, for example, provide predetermined areas of improved fluid acquisition, such as, e.g., by providing predetermined unimpeded fluid pathways to and into the absorbent member. In certain embodiments, one or more zones can be arranged to provide benefits such as regional fluid control, cleaner insertion when the tampon is inserted digitally, and/or to provide visual information to a user, such as, e.g., a perception of one or more leakage barriers, controlled fluid absorption, and/or other information related to the tampon.

As used herein, the term "tampon" refers to any type of absorbent structure that is inserted into the vaginal canal for the absorption of fluid therefrom. Typically, tampons are constructed from an absorbent material that has been compressed into a vaginally insertable shape.

As used herein, the terms "pledget" or "tampon pledget" are intended to be interchangeable and refer to a construction of absorbent material prior to the compression of such construction into a tampon.

As used herein, the terms "vaginal cavity," "within the vagina," and "vaginal interior," are intended to be synonymous and refer to the internal genitalia of the human female in the pudendal region of the body. The term "vaginal canal" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal canal" as used herein.

As used herein, "vaginally insertable shape" refers to the geometrical form of the absorbent tampon after compression. The tampon can be compressed into a generally cylindrical configuration in the radial direction along the longitudinal and/or lateral axes, axially, or in both the radial and axial directions. An example of a typical compressed tampon is one which is about 10-16 mm wide and about 30-55 mm long depending on absorbency. While the tampon may be compressed into a substantially cylindrical configuration, other shapes are possible. These may include shapes having a cross section that can be described as rectangular, triangular, trapezoidal, semi-circular, hourglass, or other suitable shapes. In certain embodiments, a tampon can have an asymmetric insertion end, such as, e.g., tampons disclosed in U.S. patent application Ser. Nos. 11/526,041 and 11/525,513.

As used herein, a first material can "substantially cover" a second material when the first material covers at least about 75%, such as, e.g., at least about 90%, of the surface area of the second material.

The term "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

The term "rolled" as used herein, refers to the configuration of the compressed absorbent member after winding the absorbent material in a spiral round and round upon itself.

The term "folded" as used herein, refers to the configuration of the compressed absorbent member that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, the term "fluid pervious" refers to the property of a material and can be characterized by the ability to carry fluid or moisture, such as by capillary action, prior to any post-processing step, such as aperturing. Therefore, for example, an untreated woven or nonwoven material is fluid pervious and a thermoplastic film is not. A nonwoven material can permit fluid flow via the interstices between fibers, such as, e.g., by capillary action and/or via a pressure differential from one side of the nonwoven to the other such as the pressure experienced by a tampon in use.

As used herein, the term "fluid impervious" refers to the property of a material and can be characterized by the ability to substantially impede the passage of fluid or moisture prior to any post-processing step, such as aperturing.

As used herein, the term "aperture" refers to a macroscopic opening or "hole" as distinct from inherent pores or interstices of a material, such as inherent pores or interstices of foams or nonwoven materials, for example. A macroscopic opening is visible to the naked eye of an observer having 20/20 vision at a distance of 45 cm in lighting at least equal to the illumination of a standard 100 watt incandescent white light bulb.

As used herein, the term "three-dimensional aperture" refers to an aperture having a greater thickness proximate an aperture than at a non-apertured point on the overwrap under zero compression. For example, in certain embodiments, a three-dimensional aperture can include a macroscopic opening or hole having one or more protuberances or sidewalls projecting generally outwardly from the surface of the web under zero compression. In certain embodiments, a three-dimensional aperture can include one or more sidewalls substantially extending outwardly form the surface of the web around the periphery of the aperture under zero compression. A three-dimensional aperture typically has a ratio of sidewall height to material thickness greater than one, such as, e.g., greater than about 1.5, greater than about 2, greater than about 2.5, or greater than about 3. Exemplary three-dimensional apertures are described in, e.g., U.S. patent application Ser. No. 11/708,296.

As used herein, the term "zone" refers to an area set off as distinct from surrounding or adjoining areas. Thus, for example, an overwrap having uniformly spaced apertures, each of which are the same size, over the entire surface of the overwrap cannot be considered to have any zones of apertures. Moreover, for example, in an overwrap having uniformly spaced apertures, each of which are the same size, a single aperture and locally surrounding material cannot be considered a zone of apertures because that single aperture and locally surrounding material are not distinct from surrounding or adjoining areas.

As used herein, the term "color" includes any color, such as, e.g., white, black, red, orange, yellow, green, blue, violet, brown, and/or any other color.

As used herein, the term "image" refers to any type of mark, figure, picture, illustration, symbol, icon, pattern, or any other indicia having a purpose of providing information, such as, e.g., source information and/or a signal or guide, to the consumer.

Tampons having an overwrap covering at least a portion of the exterior surface of the compressed absorbent member are provided. In certain embodiments, the overwrap can include one or more zones of apertures therein. In addition, the one or more zones of apertures can be spaced apart from one another. The one or more zones of apertures can provide, for example, predetermined areas of fluid control and/or visible information to a user, such as, e.g., information about fluid absorption, a "clean" finger during digital insertion, benefits of the tampon, and/or other information that can be useful to a user, such as, e.g., source information, absorbency level, and/or other signals or guides.

FIG. 1 shows one embodiment of an absorbent tampon 10 of the present invention. A compressed absorbent member 20 (sometimes referred to as the "absorbent core") of the tampon 10 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 1, the overwrap can include a first zone 70 having a plurality of apertures 90 and a second zone 80 having a plurality of apertures 90. In certain embodiments, the first zone 70 and the second zone 80 can be spaced apart. In addition, as shown in FIG. 1, the first zone 70 and the second zone 80 can be separated by an aperture-free zone 100. In certain embodiments, the first zone 70 and the second zone 80 can be arranged to provide channels of apertures 90, such as, e.g., with the first zone 70 providing a first channel of apertures 90 and the second zone 80 providing a second channel of apertures 90. As shown in FIG. 1, the channels of apertures 90 can be provided along the longitudinal axis L of the compressed absorbent member 20 and can be separated by an aperture-free zone 100. In addition, or alternatively, in certain embodiments, the first zone 70 and/or second zone 80 can have a first end 110 that can correspond to the insertion end 30 of the compressed absorbent member 20 and/or a second end 120 that can correspond to the withdrawal end 40 of the compressed absorbent member 20.

Figure 2:
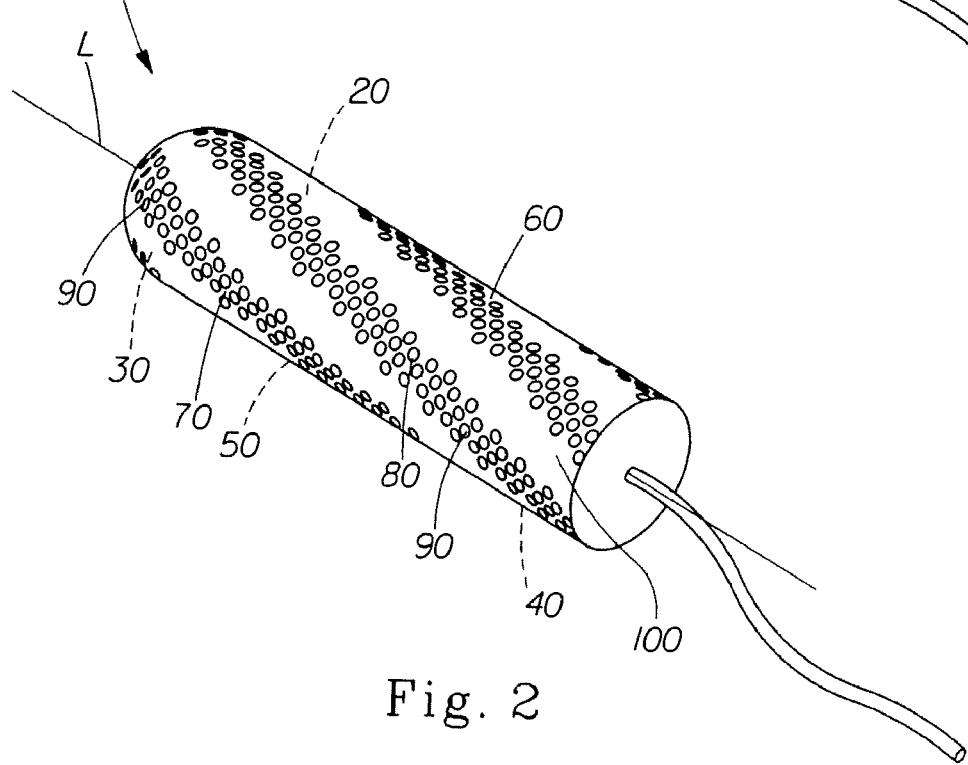
FIG. 2 is a perspective view of one embodiment of the present invention.

FIG. 2 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 2, the overwrap can include a first zone 70 having a plurality of apertures 90 and a second zone 80 having a plurality of apertures 90. In certain embodiments, the first zone 70 and the second zone 80 can be spaced apart. In addition, as shown in FIG. 2, the first zone 70 and the second zone 80 can be separated by an aperture-free zone 100. In certain embodiments, the first zone 70 and the second zone 80 can be arranged to provide channels of apertures 90, such as, e.g., with the first zone 70 providing a first channel of apertures 90 and the second zone 80 providing a second channel of apertures 90. As shown in FIG. 2, the channels of apertures 90 can be provided around the perimeter of the compressed absorbent member 20 and can be separated by an aperture-free zone 100.

Figure 3:
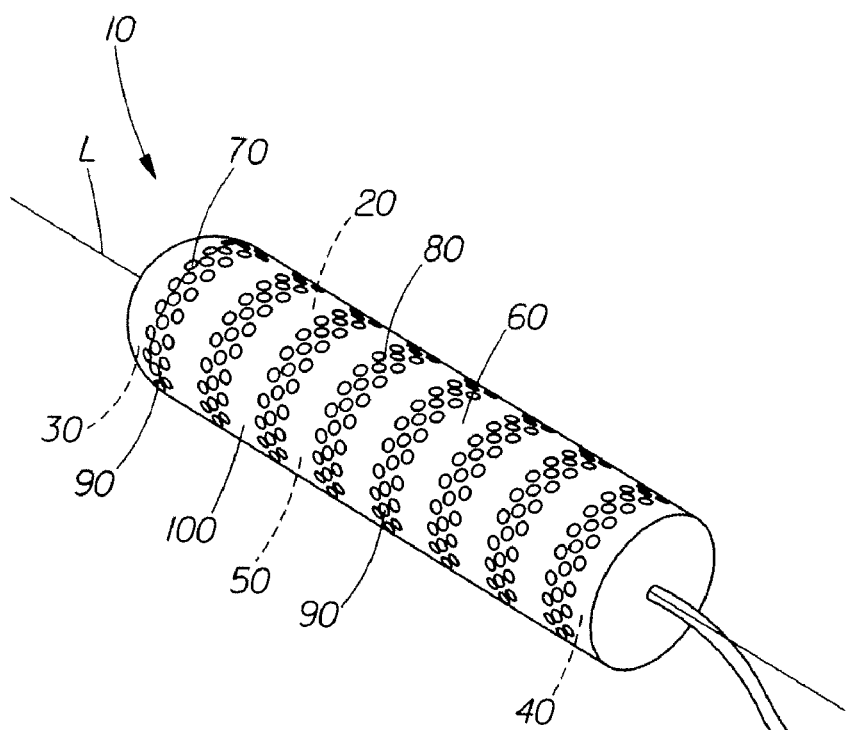
FIG. 3 is a perspective view of one embodiment of the present invention.

FIG. 3 shows one embodiment of an absorbent tampon 10 of the present invention. A compressed absorbent member 20 (sometimes referred to as the "absorbent core") of the tampon 10 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 3, the overwrap can include a first zone 70 having a plurality of apertures 90 and a second zone 80 having a plurality of apertures 90. In certain embodiments, the first zone 70 and the second zone 80 can be spaced apart. In addition, as shown in FIG. 3, the first zone 70 and the second zone 80 can be separated by an aperture-free zone 100. In certain embodiments, the first zone 70 and the second zone 80 can be arranged to provide channels of apertures 90, such as, e.g., with the first zone 70 providing a first channel of apertures 90 and the second zone 80 providing a second channel of apertures 90. As shown in FIG. 3, the channels of apertures 90 can be provided around the periphery of the tampon 10, such as, e.g., substantially perpendicular to the longitudinal axis L.

Figure 4:
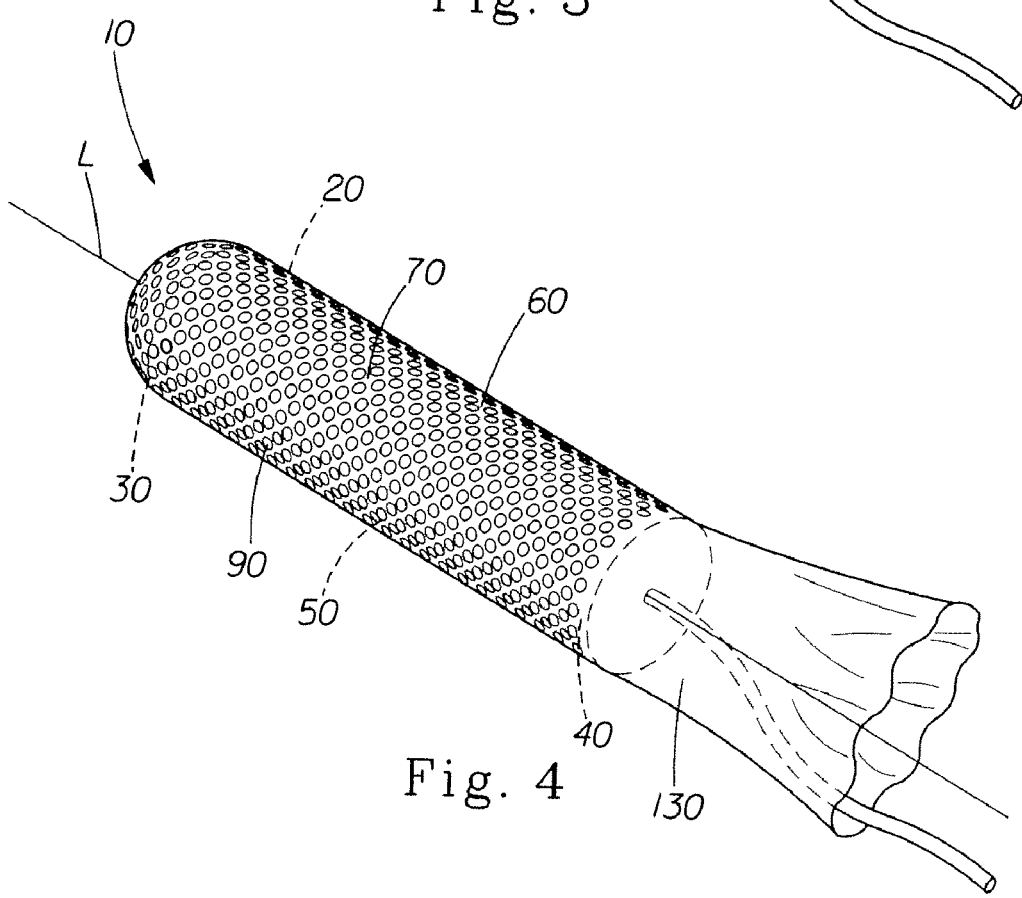
FIG. 4 is a perspective view of one embodiment of the present invention.

FIG. 4 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. In certain embodiments, the overwrap 60 can extend beyond the withdrawal end 40 to provide an extension 130. The extension 130 can function, for example, as a skirt portion and/or finger cover. As shown in FIG. 4, the overwrap can include a first zone 70 having a plurality of apertures 90 that can be aligned with at least a portion of the exterior surface of the compressed absorbent member 20. In addition, as shown in FIG. 4, the extension 130 can be substantially aperture-free.

Figure 5:
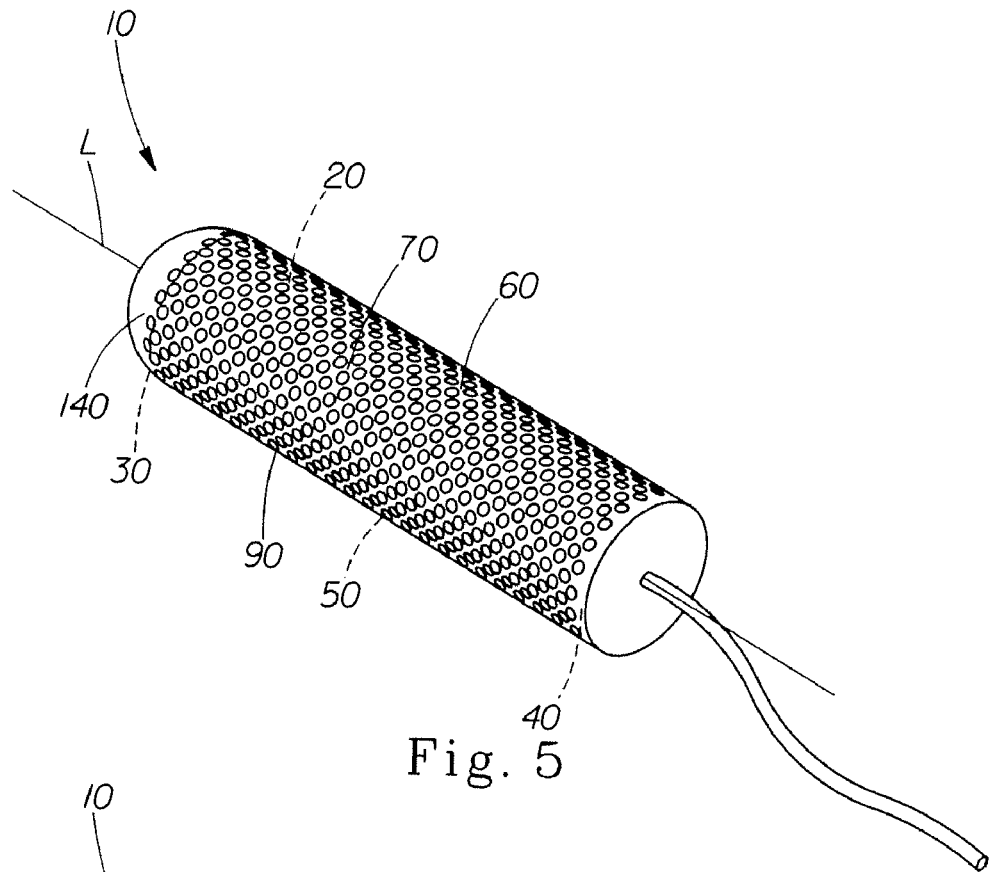
FIG. 5 is a perspective view of one embodiment of the present invention.

FIG. 5 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. In certain embodiments, the overwrap 60 can extend over the insertion end 40 to provide an extension 140, such as, e.g., an extension 140 that can function to cover at least a portion of the insertion end 40. As shown in FIG. 5, the overwrap can include a first zone 70 having a plurality of apertures 90 that can be aligned with at least a portion of the exterior surface of the compressed absorbent member 20. In addition, as shown in FIG. 5, the extension 140 can be substantially aperture-free.

Figure 6:
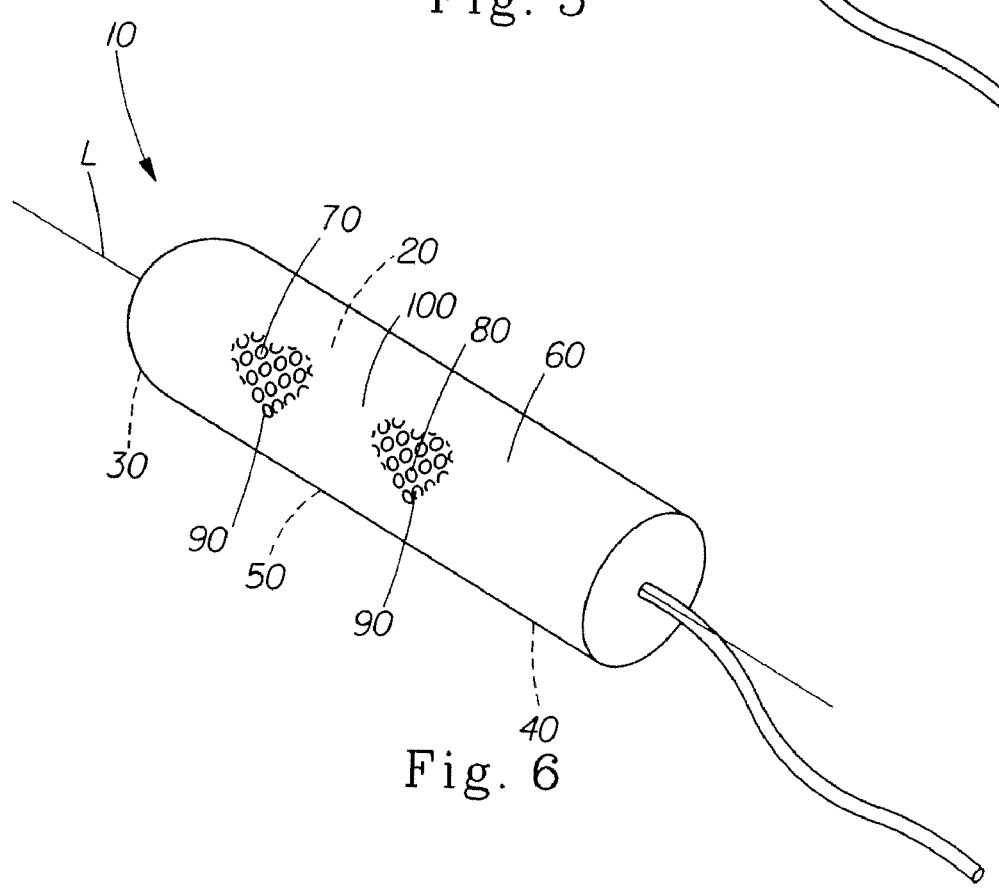
FIG. 6 is a perspective view of one embodiment of the present invention.

FIG. 6 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 6, the overwrap can include a first zone 70 having a plurality of apertures 90 and a second zone 80 having a plurality of apertures 90. In certain embodiments, the first zone 70 and the second zone 80 can be spaced apart. In addition, as shown in FIG. 6, the first zone 70 and the second zone 80 can be separated by an aperture-free zone 100. In certain embodiments, the first zone 70 and/or the second zone 80 can be provided to communicate information to a user prior to use. As shown in FIG. 6, the first zone 70 and/or the second zone 80 can include one or more images.

Figure 7:
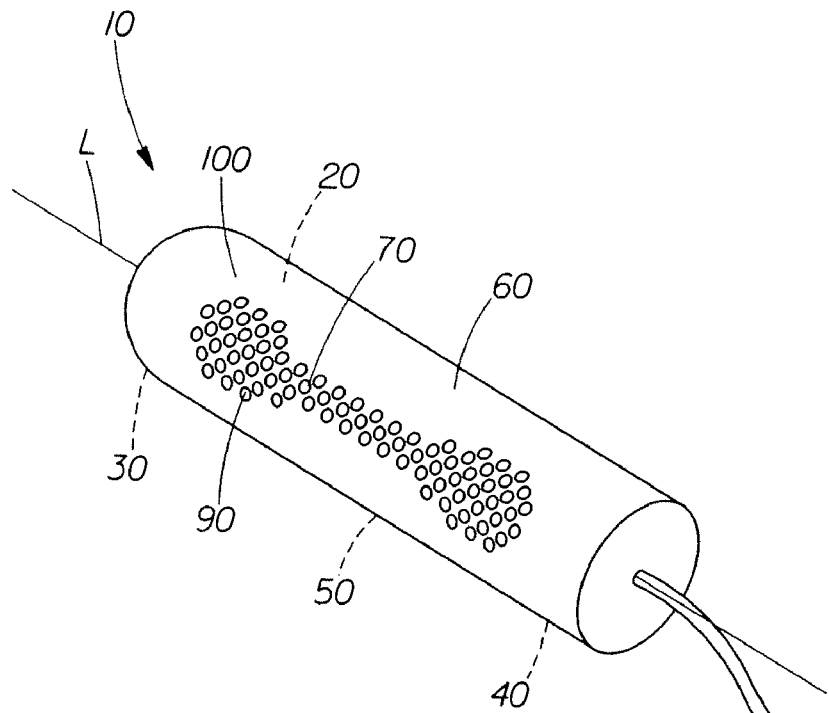
FIG. 7 is a perspective view of one embodiment of the present invention.

FIG. 7 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 7, the overwrap can include a first zone 70 having a plurality of apertures 90. In certain embodiments, the first zone 70 can be provided to communicate one or more features of the tampon 10 to a user prior to use. As shown in FIG. 7, the first zone 70 can be provided to indicate a region of enhanced absorbency. In certain embodiments, the tampon 10 can include a second zone, such as, e.g., a second zone that can be on the opposite side of the tampon 10 from the first zone 70. In addition, the second zone can be the same, substantially the same, and/or different as the first zone 70.

Figure 8:
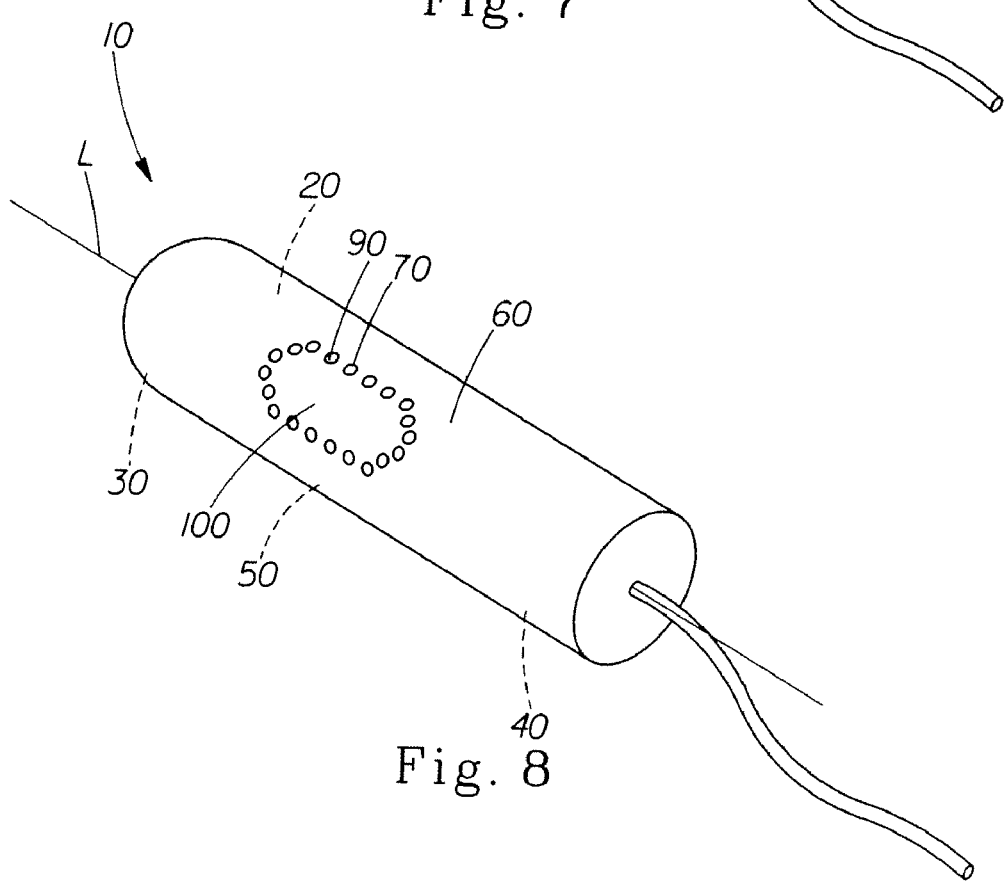
FIG. 8 is a perspective view of one embodiment of the present invention.

FIG. 8 shows one embodiment of an absorbent tampon 10 of the present invention. A compressed absorbent member 20 can have an insertion end 30, a withdrawal end 40, a longitudinal axis L, and a body 50 disposed between the insertion end 30 and the withdrawal end 40. The compressed absorbent member 20 has an exterior surface that can be at least partially covered by an overwrap 60. As shown in FIG. 8, the overwrap can include a first zone 70 having a plurality of apertures 90. In certain embodiments, the first zone 70 can be provided to communicate one or more features of the tampon 10 to a user prior to use. As shown in FIG. 8, the first zone 70 can be provided in the form of a line, such as, e.g., a line that can be disposed in the outline of a shape. In addition, in certain embodiments, as shown in FIG. 8, the zone can be provided in one or more lines that can, e.g., form the outline of a shape, and the interior of the shape can be an aperture-free zone 100. The aperture-free zone 100 can include one or more images, such as, e.g., one or more images that can provide information to a user, such as, e.g., source information, absorbency level, and/or other signals or guides. In certain embodiments, the tampon 10 can include a second zone, such as, e.g., a second zone that can be on the opposite side of the tampon 10 from the first zone 70. In addition, the second zone can be the same, substantially the same, and/or different as the first zone 70.

In certain embodiments, the one or more zones can be disposed to provide predetermined zones of fluid control. For example, zones can be provided to control fluid differently in different regions, such as, e.g., zones with apertures of a first size in one region, zones with apertures of a second size in a second region, and/or aperture-free zones. The first size and the second size can be the same, substantially the same, and/or different. In certain embodiments, a zone can have apertures of a single size and/or shape. Alternatively, a zone can have apertures of one or more sizes and/or one or more shapes. In certain embodiments, a first zone having a plurality of apertures and a second zone having a plurality of apertures can be identified due to the zones being spaced apart from one another, such as, e.g., when the first zone and the second zone are substantially separated by an aperture-free zone.

Zones can be spaced apart from one another in any suitable manner. In certain embodiments, a first zone and a second zone are spaced apart from one another such that the zones are visually separated from one another. In addition, or alternatively, a first zone and a second zone can be spaced apart from one another by a distance greater than the maximum spacing between adjacent apertures within the first zone and/or the second zone.

Zones can be any suitable size to achieve the intended purpose of the zone. For example, in certain embodiments, a single zone can be at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater of the surface area of the overwrap. When an overwrap includes more than one zone, one or more of the individual zones can have substantially the same area, and/or one or more of the individual zones can have a different area. For example, in certain embodiments, the overwrap can include a first zone and a second zone that can be substantially the same area of the overwrap and a third zone that can be a larger or smaller area than the first zone or second zone.

In certain embodiments, one or more zones can be arranged to provide channels, lines, or stripes of apertures on the overwrap. Such channels, lines, or stripes can be provided in any suitable configuration, such as, e.g., in a straight, twisted, or wavy configuration, and in any suitable location on the overwrap with respect to the compressed absorbent member, such as, e.g., along the longitudinal axis and/or around the periphery, such as, e.g., substantially perpendicular to the longitudinal axis. In certain embodiments, the channels, lines, or stripes of apertures can be provided along the length of the tampon from the insertion end to the withdrawal end. In addition, or alternatively, the channels, lines, or stripes of apertures can be spaced apart from one another, such as, e.g., substantially separated from one another by an aperture-free zone. In certain embodiments, a zone can include apertures that can be arranged in one or more lines, such as, e.g., one or more lines provided in the outline of a shape.

As discussed above, the overwrap can include an extension, such as, e.g., an extension extending beyond the body of the tampon along the longitudinal axis. In certain embodiments, the extension can be substantially aperture-free, such as, e.g., when the extension can function as a finger cover during digital insertion and/or when the extension extends over the withdrawal end of the tampon, such as, e.g., to function as a cover for the withdrawal end. Alternatively, the extension can include one or more zones of apertures, such as, e.g., when the extension extends over the insertion end of the tampon, such as, e.g., to form a cover for the insertion end.

In certain embodiments, one or more zones can be provided to communicate information to a user. A zone can be designed to communicate information in any suitable manner, such as, e.g., by the zone location, zone shape and/or size, and/or aperture size. Any suitable information can be provided, such as, e.g., information about the location or perceived location of a fluid barrier, a path of fluid flow, and/or a zone of improved absorbency. In certain embodiments, a zone can be provided to communicate an image, a decorative pattern, a source identifier, absorbency level, and/or a logo. In addition, or alternatively, one or more zones can be provided to allow a user to visibly detect the color of the compressed absorbent member through the apertures of the zone. For example, in certain embodiments, at least a portion of the compressed absorbent member can include one or more colors that can be viewable through one or more apertures of a zone. In addition, the zone can be a color that is the same or different as the color viewable through one or more apertures of the zone, such as, e.g., the color of the compressed absorbent member. In certain embodiments, the compressed absorbent member can be a first color viewable through one or more apertures of the zone and the overwrap can be a second color in the zone area adjacent to the apertures of the zone. Color can be provided in any suitable manner, such as, e.g., by dying, spraying, printing, coating, and/or any other suitable manner.

Zones can be provided in any suitable area of the overwrap. For example, one or more zones can be provided on the overwrap such that the one or more zones correspond to the body of the compressed absorbent member in the finished tampon. In addition, or alternatively, one or more zones can be provided on the overwrap such that the one or more zones correspond to the insertion end, the withdrawal end, and/or a finger cover. In certain embodiments, one or more zones can be registered to features of the compressed absorbent member, such as, e.g., grooves, ridges, center absorbency regions, or other suitable features.

Apertures can be of virtually any shape and size. In certain embodiments, apertures can be generally round or oblong shaped, in a regular pattern of spaced apart openings. The apertures can each have any suitable area, such as, e.g., an area of from about 0.3 mm$^2$ to about 4 mm$^2$, such as, e.g., about 2 mm$^2$, such as, e.g., about 1 mm$^2$, and can form an open area of between about 1% and about 25%, such as, e.g., between about 2% and about 20%, such as, e.g., an open area between about 10% and about 15%. In certain embodiments, the apertures can be provided in non-repeating and/or non-regular patterns that can be random and/or can have various shapes and sizes.

The overwrap can be a fluid pervious overwrap, such as, e.g., an overwrap including a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber. The basis weight of the nonwoven overwrap prior to forming apertures can be any suitable weight, such as, e.g., from about 5 to about 60 grams per square meter (gsm), such as, e.g., from about 10 to about 30 gsm. Synthetic fibers, if used, can have hydrophobic and/or hydrophilic finishes, although, as mentioned above, in certain embodiments, the fibers of the nonwoven can be rendered hydrophobic relative to the absorbent member.

Alternatively, or in addition, the overwrap can be a fluid impervious overwrap, such as, e.g., a plastic material, such as, e.g., one or more polymeric mesh materials.

As set forth herein, in certain embodiments, the overwrap can be hydrophobic relative to the compressed absorbent member. Hydrophobicity can be inherent due to the material properties of the overwrap material, or the overwrap can be rendered hydrophobic by suitable treatment of an otherwise hydrophilic material. For example, the overwrap can comprise one or more fibers that are inherently more hydrophobic than the compressed absorbent member, such as, e.g., polypropylene spunbond and/or conjugate fibers, such as bicomponent polyethylene/polypropylene fibers and/or bicomponent polyethylene/polyester fibers.

Alternatively, or in addition, the overwrap can contain hydrophilic fibers, such as, e.g., rayon or a blend of rayon/cotton, that can, in certain embodiments, be rendered hydrophobic by a suitable treatment. Any suitable treatment can be employed, such as, e.g., a coating of a suitable material sufficient to render the overwrap sufficiently hydrophobic. For example, surface treatments can include applied coatings of silicone, such as Dow Corning 108® silicone, available from the Dow Corning Co. Inc., Midland, Mich.; or Sucrose Esters of Fatty Acids (SEFA), available from the Procter & Gamble Co., Inc., Cincinnati, Ohio, polyolefin waxes, or NALAN® available from DuPont, Wilmington Del. Such coatings can render the overwrap hydrophobic, or highly hydrophobic. The application of a suitable surface treatment can be achieved by spraying, slot coating, immersion and other suitable methods. The amount of coating can be varied as needed to render the overwrap sufficiently hydrophobic relative to the compressed absorbent member. In one embodiment, a 1% by weight coating of SEFA can be utilized. Sufficient relative hydrophobicity is achieved when fluid such as menses is absorbed into the compressed absorbent member in use, and is sufficiently desorbed from the overwrap so as to partition the fluid into the core and away from the overwrap.

In certain embodiments, the overwrap can be hydrophilic relative to the compressed absorbent member. Hydrophilicity can be inherent due to the material properties of the overwrap material, or the overwrap can be rendered hydrophobic by suitable treatment. For example, the overwrap can comprise one or more fibers that are inherently more hydrophobic than the compressed absorbent member, such as, e.g., rayon and/or cotton, and/or can be rendered hydrophobic by a suitable treatment.

The overwrap can be joined to the absorbent material by any variety of means. The overwrap can be joined to itself or to the absorbent material. For example, one portion of overwrap can be joined to an opposed portion of the overwrap or the absorbent member using any suitable adhesive or heat/pressure bonding means. Such adhesive can extend continuously along the length of attachment or it can be applied in a non-continuous fashion at discrete intervals. Heat bonding includes thermally bonding, fusion bonding, or any other suitable means for joining such materials. Alternatively, the overwrap may be joined to the absorbent material by stitching. Such stitching may use natural or synthetic thread.

The compressed absorbent member can be formed in any suitable manner. In certain embodiments, the absorbent material can be joined to the overwrap and can be rolled and/or folded, compressed and optionally heat conditioned in any suitable conventional manner. In certain embodiments, after rolling or folding and compression, the apertured overwrap can cover the exterior surface of the compressed absorbent member and can also be embedded in the interior folds of the compressed absorbent member. That is, in certain embodiments, the apertured overwrap can permeate the interior of the compressed absorbent member.

The absorbent material can be any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911,712; 6,740,070; 6,887,266; and 6,953,456. A typical size for absorbent material prior to compression can be from about 30 mm to about 100 mm in length and from about 30 mm to about 80 mm in width. The typical range for the overall basis weight of the absorbent material 28 is from about 150 gsm to about 1250 gsm depending upon desired absorbent capacity. The materials for the tampon can be formed into a fabric, web, or batt that is suitable for use in the absorbent material by any suitable process such as airlaying, carding, wetlaying, hydroentangling, needling or other known techniques. In certain embodiments, the absorbent material can be a single pledget that can be compressed to form a tampon.

The absorbent material can be a laminar structure comprised of integral or discrete layers. In other embodiments, the pad need not have a layered structure at all. The absorbent material may comprise a folded structure or may be rolled. The resulting compressed absorbent member of the tampon can be constructed from a wide variety of liquid-absorbing materials commonly used in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

Any suitable pressures and temperatures for compression can be used. In certain embodiments, the absorbent material and the overwrap can be compressed in the radial direction and optionally axially by any suitable means. While a variety of techniques are known and acceptable for these purposes, a tampon compressor machine available from Hauni Machines, Richmond, Va., can be suitable.

As set forth herein, in certain embodiments, the tampon can be a tampon having a folded construction. Alternatively, the tampon can be a tampon having a radially compressed rolled construction. The tampon can be constructed by rolling and radially compressing a pledget. The pledget can be rolled around a mandrel then compressed with or without the mandrel. In certain embodiments, a cavity left behind after the mandrel is removed can provide a finger pocket. The tampon can also be constructed by pressing a pledget, such as, for example, a cylindrical pledget, in forming dies with a pushrod. A cavity that can be a finger pocket can be formed in part of the blank pressed against a convex in the forming dies or the pushrod.

The tampon can additionally include a withdrawal member. The withdrawal member can be any suitable configuration, such as, e.g., one or more cords, strings, finger covers, ribbons, an extension of a material of the device, or combinations thereof. The withdrawal member can be made of any suitable material, such as, e.g., cotton and rayon. The withdrawal member can optionally be provided with a secondary absorbent member. Suitable secondary absorbent members are described in, e.g., U.S. Pat. No. 6,258,075.

In certain embodiments, the tampon can include a finger pocket and/or a finger indent at the withdrawal end of the tampon, such as, e.g., to aid in insertion described in, such as, e.g., U.S. Pat. No. 6,283,952. In certain embodiments, at least a portion of the withdrawal member can be at least partially disposed in the finger pocket and/or the finger indent. The finger pocket or the finger indent may be hidden in the finished tampon and appear once the user prepares the device for insertion at least partially extending the withdrawal member, and/or loosening the withdrawal end of the tampon by moving the withdrawal cord. In addition, or alternatively, the tampon can include an overwrap that extends from the withdrawal end and forms a finger cover. In certain embodiments, the tampon can include an overwrap that extends from the withdrawal end and forms an absorbent skirt. In addition, the excess of the overwrap can be at least partially disposed in a finger pocket or a finger indent and can be pulled out to provide a finger cover or an absorbent skirt when the user prepares the tampon for insertion. In certain embodiments, the excess of the overwrap can be joined with the withdrawal cord and disposed in the finger pocket or the finger indent along with the withdrawal cord, such as, for example, in U.S. patent application Ser. Nos. 11/525,553 and 11/525,730.

While several methods of making the tampon of the present invention should be apparent to one of skill in the art in light of the disclosure herein, following is a description of one method of making a tampon of the present invention.

In certain embodiments, the process for making a tampon can include the steps of providing an absorbent material having a first surface opposed to a second surface and an insertion end opposed to a withdrawal end, and providing a overwrap, such as, e.g., an overwrap including one or more nonwoven materials having a material thickness, the overwrap having one or more zones of apertures therein. The overwrap can be wrapped or folded about the absorbent material to cover at least a portion of, and/or or substantially cover, one or more surfaces. The wrapped absorbent can be rolled or folded and/or compressed to form a compressed absorbent member having a vaginally insertable shape. Upon compression, the overwrap can cover at least a portion and/or substantially cover the exterior surface of the compressed absorbent member.

The apertures can be formed at any suitable point during the process for making a tampon. For example, in certain embodiments, the overwrap can be apertured prior to the tampon forming process, such as, e.g., using separate machinery. Alternatively, the overwrap can be provided on the tampon converting line in unmodified form and can be apertured during the tampon forming process, such as, e.g., prior to, during, or after the formation of the tampon pledget. In certain embodiments, the overwrap can be apertured on the tampon converting line and the apertures can be registered to the tampon pledget prior to compression.

In addition, apertures can be formed in any suitable manner. Suitable aperturing techniques include, for example, rotary knife aperturing, such as, e.g., disclosed in U.S. Patent Appln. Publication No. 2006/0087053; hot needle aperturing, such as, e.g., disclosed in International Patent Appln. WO 2005/011936 and/or U.S. Pat. No. 6,849,319; stretch aperturing, such as, e.g., disclosed in U.S. Pat. No. 5,628,097; hydroentangling, such as, e.g., disclosed in U.S. Pat. No. 4,024,312; laying or impressing fibers over a three-dimensionally structured screen or mesh such as, e.g., described in U.S. Pat. Nos. 4,024,612, 5,503,715, and/or 6,270,623, and/or by any other suitable manner.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial tampon comprising:
   a compressed absorbent member having an insertion end, a withdrawal end, a longitudinal axis, and a body disposed between the insertion end and the withdrawal end, the body having a perimeter disposed substantially perpendicularly to the longitudinal axis, the body having an exterior surface;
   an overwrap covering at least a portion of the exterior surface, the overwrap comprising a fluid pervious material;
   wherein the overwrap comprises a first zone and a second zone, the first zone having a plurality of apertures of a first diameter and the second zone having a plurality of apertures of a second diameter, the first diameter being different from the second diameter, the first zone and the second zone being spaced apart from one another by a distance greater than a maximum spacing between adjacent apertures within the first zone and/or the second zone, and
   wherein the first zone and the second zone are substantially separated by a third zone, the third zone being aperture-free.

2. The tampon of claim 1, wherein the first zone and the second zone have a length and a width, the length being greater than the width.

3. The tampon of claim 2, wherein the length of the first zone and the length of the second zone are substantially aligned with the longitudinal axis.

4. The tampon of claim 2, wherein the length of the first zone and the length of the second zone are disposed about the periphery.

5. The tampon of claim 1, wherein the first zone and the second zone have a first end corresponding to the insertion end and a second end corresponding to the withdrawal end.

6. The tampon of claim 1, wherein the third zone has a width and a length, the length being greater than the width.

7. The tampon of claim 6, wherein the width of the third zone is greater than a maximum spacing between adjacent apertures within the first zone and/or the second zone.

8. The tampon of claim 1, wherein the first zone further includes a plurality of apertures of a third diameter.

9. The tampon of claim 1, wherein the second zone further includes a plurality of apertures of a fourth diameter.

10. The tampon of claim 1, wherein the first zone, the second zone, and the third zone are arranged to provide channels of apertures separated by an aperture-free zone.

11. The tampon of claim 1, wherein the overwrap further comprises at least one extension extending beyond the body along the longitudinal axis, and wherein the extension extends past the withdrawal end of the tampon to form a finger cover.

12. A catamenial tampon comprising:
   a compressed absorbent member having an inner region and an exterior surface, the compressed absorbent member comprising one or more absorbent materials;
   an overwrap covering at least a portion of the exterior surface of the compressed absorbent member, the overwrap comprising a fluid pervious material;
   wherein the overwrap comprises a first zone and a second zone, the first zone having a plurality of apertures of a first diameter and the second zone having a plurality of apertures of a second diameter, the first diameter being different from the second diameter, the first zone and the second zone being spaced apart from one another by a distance greater than a maximum spacing between adjacent apertures within the first zone and/or the second zone, the first zone being provided to communicate one or more features of the tampon to a user prior to use, and wherein the first zone is substantially bounded by one or more substantially aperture-free zones.

13. The tampon of claim 12, wherein the one or more features is a fluid barrier, a path of fluid flow, an image, a decorative pattern, a logo, and/or a zone of improved absorbency.

14. The tampon of claim 12, wherein the compressed absorbent member is a first color, the first color being viewable through one or more apertures of the first zone.

* * * * *